(12) United States Patent
Kaddurah-Daouk et al.

(10) Patent No.: US 7,285,573 B2
(45) Date of Patent: Oct. 23, 2007

(54) USE OF CREATINE OR CREATINE ANALOGS FOR THE TREATMENT OF DISEASES OF THE NERVOUS SYSTEM

(75) Inventors: Rima Kaddurah-Daouk, Belmont, MA (US); Ghaleb Daouk, Belmont, MA (US); M. Flint Beal, New York, NY (US)

(73) Assignees: Avicena Group, Inc., Palo Alto, CA (US); The General Hospital Corp., Boston, MA (US)

( * ) Notice: Subject to any disclaimer, the term of this patent is extended or adjusted under 35 U.S.C. 154(b) by 123 days.

(21) Appl. No.: 10/718,846

(22) Filed: Nov. 21, 2003

(65) Prior Publication Data

US 2004/0106680 A1    Jun. 3, 2004

Related U.S. Application Data

(63) Continuation of application No. 08/853,174, filed as application No. PCT/US95/14567 on Nov. 7, 1995, now Pat. No. 6,706,764, which is a continuation of application No. 08/336,388, filed on Nov. 8, 1994, now abandoned.

(51) Int. Cl.
*A01N 37/52* (2006.01)

(52) U.S. Cl. ...................... 514/565; 514/631

(58) Field of Classification Search ............... 514/565, 514/631
See application file for complete search history.

(56) References Cited

U.S. PATENT DOCUMENTS

| 4,788,179 | A | * | 11/1988 | Flohe et al. .................. 514/19 |
| 5,091,404 | A | | 2/1992 | Elgebaly |
| 5,321,030 | A | | 6/1994 | Kaddurah-Daouk et al. |
| 5,324,731 | A | | 6/1994 | Kaddurah-Daouk et al. |
| 5,492,930 | A | | 2/1996 | Coffin |
| 5,741,661 | A | | 4/1998 | Goldin et al. |
| 6,169,115 | B1 | | 1/2001 | Kaddurah-Daouk |

FOREIGN PATENT DOCUMENTS

| WO | WO 90/09192 | 8/1990 |
| WO | WO 92/08456 | 5/1992 |
| WO | WO 94/16687 | 8/1994 |
| WO | WO 94/17794 A1 | 8/1994 |

OTHER PUBLICATIONS

Annesley, T., et al., "Cyclocreatine Phosphate as a Substitute for Creatine Phosphate in Vertebrate Tissue, Energetic Considerations," *Biochem. Biophys. Res. Commun.*, 1977; 74:185-90.

Annesley, T., et al., "Formation and Utilization of Novel High Energy Phosphate Reservoirs in Ehrlich Ascites Tumor Cells," *J. Biol. Chem.*, 1978; 253(22):8120-5

Beal, M., "Aging, Energy, and Oxidative Stress in Neurodegenerative Diseases," *Ann. Neurol.*, 1995; 38:357-66.

Beal, M., "Does Impairment of Energy Metabolism Result in Excitotoxic Neuronal Death in Neurodegenerative Illnesses?" *Ann. Neurol.*, 1992; 31:119-30.

Beal, M. et al., "Age-Dependent Striatal Excitotoxic Lesions Produced by the Endogenous Mitochondrial Inhibitor Malonate," *J. Neurochem.*, 1993; 61:1147-50.

Bertolini, et al., Chemical Abstracts AN 1982:49622.

Brady, S., et al., "Nerve-Specific Enolase and Creatine Phosphokinase in Axonal Transport: Soluble Proteins and the Axoplasmic Matrix," *Cell*, 1981; 23:515-23.

Brouillet, E., et al., "Chronic Mitochondrial Energy Impairment Produces Selective Striatal Degeneration and Abnormal Choreiform Movements in Primates," *PNAS*, 1995; 92:7105-9.

Browne, S., et al., "Oxidative Damage and Metabolic Dysfunction in Huntington's Disease: Selective Vulnerability of the Basal Ganglia," *Ann. Neurol.*, 1997; 41:646-53.

Burbaeva, G.S., et al., "Decreased Level of Immunoreactive Phosphokinase BB Isoenzymes in the Brain of Patients with Schizophrenia and Senile Dementia of the Alzheimer Type," *Zh. Nevropatol. Psikhiatr Im S S Korsakova*, 1990; 90(7):85-7.

(Continued)

*Primary Examiner*—Mark L. Shibuya
(74) *Attorney, Agent, or Firm*—Lahive & Cockfield, LLP; Elizabeth A. Hanley, Esq.; Cynthia M. Sooros, Esq.

(57) ABSTRACT

The present invention relates to the use of creatine compounds including creatine, creatine phosphate or analogs of creatine, such as cyclocreatine, for treating diseases of the nervous system. Creatine compounds can be used as therapeutically effective agents against a variety of diseases of the nervous system such as diabetic and toxic neuropathies, peripheral nervous system diseases, Alzheimer's disease, Parkinson's disease, stroke, Huntington's disease, amyotropic lateral sclerosis, motor neuron disease, traumatic nerve injury, multiple sclerosis, dysmyelination and demyelination disorders, and mitochondrial diseases. The creatine compounds which can be used in the present method include (1) creatine, creatine phosphate and analogs of these compounds which can act as substrates or substrate analogs for creatine kinase; (2) bisubstrate inhibitors of creatine kinase comprising covalently linked structural analogs of adenosine triphosphate (ATP) and creatine; (3) creatine analogs which can act as reversible or irreversible inhibitors of creatine kinase; and (4) N-phosphorocreatine analogs bearing non-transferable moieties which mimic the N-phosphoryl group.

8 Claims, 2 Drawing Sheets

OTHER PUBLICATIONS

Cadoux-Hudson, T., et al., "Imaging of Human Brain Creatine Kinase Activity in Vivo," *FASEB J.*, 1989; 3:2660-6.

Carter, A.J., et al., "Preincubation with creatine enhances levels of creatine phosphate and prevents anoxic damage in rat hippocampal slices," *J Neurochem.* 1995; 64(6):2691-9.

Chandler, W., et al., "Regional Creatine Kinase, Adenylate Kinase, and Lactate Dehydrogenase in Normal Canine Brain," *Stroke*, 1988; 19:251-5.

Cramer, F., et al., "Die Synthese der Argininphosphorsäure und die Reaktion von Isoureidophosphonaten mit Aminen," *Chem. Ber.*, 1962, 95:1670-82.

De Leon, M., et al., "Identification of Transcriptionally Regulated Genes After Sciatic Nerve Injury," *J. Neurosci. Res.*, 1991: 29:437-48.

Erecinska, M., et al., "ATP and Brain Function," *J. Cerebr. Bloof Flow and Metabolism*, 1989; 9:2-19.

Friedhoff, A., et al., "Creatine Kinase Isoenzyme Associated with Synaptosomal Membrane and Synaptic Vesicles," *Life Sci.*, 1977; 20:867-74.

Goodman & Gilman, The Pharmcological Basis of Therapeutics, 1980, 6$^{th}$ Ed. (MacMillan Pub.); 5-10.

Griffiths, G., et al., "Accumulation of Analog of Phosphocreatine in Muscle of Chicks Fed 1-Carboxymethyl-2-iminoimidazolidine (Cyclocreatine)," *J. Biol. Chem.*, 1976; 251(7):2049-54.

Gu, M., et al., "Mitochondrial Defect in Huntington's Disease Caudate Nucleus," *Ann. Neurol.*, 1996; 39:385-9.

Gurney, M., et al., "Motor Neuron Degeneration in Mice That Express a Human Cu,Zn Superoxide Dismutase Mutation," *Science*, 1994; 264:1772-5.

Hemmer, W., et al., "Functional Aspects of Creatine Kinase in Brain," *Dev. Neuroscience*, 1993; 15:249-260.

Hagenfeldt, L., et al., "Creatine Treatment in MELAS," *Muscle and Nerve*. 1994; 10:1236-7.

Hemmer, W., et al., "Creatine Kinase Isoenzymes in Chicken Cerebellum: Specific Localization of Brain-type Creatine Kinase in Bergmann Glial Cells and Muscle-type Creatine Kinase in Purkinje Neurons," *Eur. J. Neuroscience*, 1994; 6:538-49.

Henshaw, R., et al., "Malonate Produces Striatal Lesions by Indirect NMDA Receptor Activation," *Brain Research*, 1994; 647:161-6.

Hertz, L., et al., "Energy Metabolism at the Cellular Level of the CNS," *Can. J. Physiol. Pharmacol.*, 1992; 70:S145-57.

Ito, M., "The Cellular Basis of Cerebellar Plasticity," *Corr. Opin. Neurobiol.*, 1991; 1:616-20.

Jenkins, B., et al., "Evidence for Impairment of Energy Metabolism in Vivo in Huntington's Disease Using Localized 1H NMR Spectroscopy," *Neurology*, 1993; 43:2689-95.

Kahn, M.A., "Effect of Calcium on Creatine Kinase Activity of Cerebellum," *Histochem.*, 1976; 48:29-32.

Lillie, J., et al., "Cyclocreatine (1-Carboxymethyl-2-iminoimidazolidine) Inhibits Growth of a Broad Spectrum of Cancer Cells Derived from Solid Tumors," *Cancer Res.*, 1993; 53:3172-8.

Lim, L., et al., "Neurone-Specific Enolase and Creatine Phosphokinase are Protein Components of Rat Brain Synaptic Plasma Membranes," *J. Neurochem.*, 1983; 41:1177-82.

LoPresti, P., et al., "Direct Determination of Creatine Kinase Equilibrium Constants with Creatine or Cyclocreatine as Substrate," *Biochem. Biophys. Acta.*, 1989; 998:317-20.

Lowe, G., et al., "Evidence for an Associative Mechanism in the Phosphoryl Transfer Step Catalyzed by Rabbit Muscle Creatine Kinase," *J. Biol. Chem.*, 1980; 225(9):3944-51.

Maker, H., et al., "Regional Changes in Cerebellar Creatine Phosphate Metabolism During Late Maturation," *Exp. Neurol.*, 1973; 38:295-300.

Manos, P., et al., "Creatine Kinase Activity in Postnatal Rat Brain Development and in Cultured Neurons, Astrocytes, and Oligodendrocytes," *J. Neurochem.*, 1991; 56:2101-7.

Marletta, M., et al., "Affinity Labeling of Creatine Kinase by N-(2,3-Epoxypropyl)-N-amidinoglycine," *J. Biol. Chem.*, 1979; 254(6):1879-86.

McLaughlin, A., et al., "Specificity of Creatine Kinase for Guanidino Substrates," *J. Biol. Chem.*, 1972; 247(13):4382-8.

Molloy, G., et al., "Rat Brain Creatine Kinase Messenger RNA Levels are High in Primary Cultures of Brain Astrocytes and Oligodendrocytes and Low in Neurons," *J. Neurochem.*, 1992; 59:1925-32.

Newman, E., "Regulation of Potassium Levels by Glial Cells in the Retina," *Trends Neuroscience*, 1985; 8:156-9.

Oblinger, M., et al., "Cytotypic Differences in the Protein Composition of the Axonally Transported Cytoskeleton in Mammalian Neurons," *J. Neurol.*, 1987; 7(2):453-62.

Orlovskaia, D.D., et al., "Neuromorphology and Neurochemistry of Senile Dementias in the Light of Studies on Glial Response," *Vestn Ross Akad Med Nauk.*, 1992; 8:34-9.

Rees, et al., Chemical Abstracts AN 89:82648, US patent 4,981,774.

Reichenbach, A., "Glial K+ Permeability and CNS K+ Clearance by Diffusion and Spatial Buffering," *Acad. Sci. New York*, 1991;272-86.

Roberts, J., et al., "Higher Homolog and N-Ethyl Analog of Creatine as Synthetic Phosphagen Precursors in Brain, Heart, and Muscle, Repressors of Liver Amidinotransferase, and Substrates for Creatine Catabolic Enzymes," *J. Biol. Chem.*, 1985; 260(25):13502-8.

Roberts, J., et al., "Synthesis and Accumulation of an Extremely Stable High-Energy Phosphate Compound by Muscle, Heart, and Brain of Animals Fed the Creatine Analog, 1-Carboxyethyl-2-iminoimidazolikine (Homocyclocreatine)," *Arch. Biochem. Biophys.*, 1983; 220(2):563-71.

Rowley, G.L., et al., "On the Specificity of Creatine Kinase, New Glycocyamines and Glycocyamine Analogs Related to Creatine," *Journal of the American Chemical Society*, 1971; 93:5542-51.

Rudinger, "Peptide Hormones," 1976 (J. Parsons Ed.); 1-6.

Schiffmann, R., et al., "Childhood Ataxia with Diffuse Central Nervous System Hypomyelination," *Ann. Neurol.*, 1994; 35:331-40.

Schulthesis, et al., "Effects of Creatine on Synthesis and Release of Gamma-[3H] Aminobutyric Acid," *Journal of Neurochemistry*, 54(6):1858-63.

Schultz, J., et al., "Blockade of Neuronal Nitric Oxide Synthase Protects Against Excitotoxicity in vivo," *J. Neurosci.*, 1995; 15(12):8419-29.

Schultz, J., et al., "Inhibition of Neuronal Nitric Oxide Synthase by 7-Nitroindazole Protects Against MPTP-Induced Neurotoxicity in Mice," *J. Neurochem.*, 1995; 64:936-9.

Stadhouders, A., et al., "Mitochondrial Creatine Kinase: A Major Constituent of Pathological Inclusions Seen in Mitochondrial Myopathies," *PNAS*, 1994; 91(11):5089-93.

Wang, T., "Synthesis and Properties of N-Acetimidoyl Derivatives of Glycine and Sarcosine," *JOC*, 1974; 39(24):3591-4.

Beal, M. Flint et al, "Aminooxyacetic Acid Results in Excitotoxin Lesions by a Novel Indirect Mechanism," *Journal of Neurochemistry*, vol. 57:1068-1073 (1991).

Erecińska, Maria et al, "ATP and Brain Function," *Journal of Cerebral Blood Flow and Metabolism*, vol. 9:2-19 (1989).

Nuti, Angelo et al, "Terapia con desametazone nella Corea di Huntington: risultati preliminari," *Nuova Rivista di Neurologia*, vol. 61(6):225-227 (1991), English Abstr. only.

Roberts, Jeffrey J. et al, "Feeding a creatine analogue delays ATP depletion and onset of rigor in ischemic heart," *Am. J. Physiol.*, vol. 243:H911-H916 (1982).

Walker, James B., "Bioenergetic engineering with guanidino compounds. Loading tissues with extended-range synthetic thermodynamic buffers," *Guanidino Compounds in Biology and Medicine*, eds. P.P. De Deyn et al, John Libbey & Company Ltd., pp. 187-194 (1992).

Pettegrew, Jay W. et al., "Alterations of Cerebral Metabolism in Probable Alzheimer's Disease: A Preliminary Study," *Neurobiology of Aging*, vol. 15(1):117-132 (1994).

European Search Report for Application No. 06011215.8-2107, dated Sep. 18, 2006.

* cited by examiner

USE OF CREATINE OR CREATINE ANALOGS FOR THE TREATMENT OF DISEASES OF THE NERVOUS SYSTEM

RELATED APPLICATIONS

This application is a continuation of U.S. patent application Ser. No. 08/853,174, filed on May 7, 1997, now U.S. Pat. No. 6,706,764 which which is a national stage of PCT Application PCT/US95/14567, which was filed on Nov. 7, 1995, which claims priority to U.S. patent application Ser. No. 08/336,388, filed on Nov. 8, 1994 now abandoned. The entire contents of each of the aforementioned patent applications are hereby incorporated herein by reference.

BACKGROUND OF THE INVENTION

Creatine is a compound which is naturally occurring and is found in mammalian brain and other excitable tissues, such as skeletal muscle, retina and heart. Its phosphorylated form, creatine phosphate, also is found in the same organs and is the product of the creatine kinase reaction utilizing creatine as a substrate. Creatine and creatine phosphate can be synthesized relatively easily and are believed to be non-toxic to mammals. Kaddurah-Daouk et al. (WO 92/08456, published May 29, 1992 and WO 90/09192, published Aug. 23, 1990; U.S. Pat. No. 5,321,030; and U.S. Pat. No. 5,324,731) describe methods of inhibiting the growth, transformation and/or metastasis of mammalian cells using related compounds. Examples of compounds described by Kaddurah-Daouk et al. include cyclocreatine, b-guandidino propionic acid, homocyclocreatine, 1-carboxymethyl-2-iminohexahydropyrimidine, guanidino acetate and carbocreatine. These same inventors have also demonstrated the efficacy of such compounds for combating viral infections (U.S. Pat. No. 5,321,030). Elebaly in U.S. Pat. No. 5,091,404 discloses the use of cyclocreatine for restoring functionality in muscle tissue. Cohn in PCT publication No. WO94/16687 described a method for inhibiting the growth of several tumors using creatine and related compounds.

The nervous system is an unresting assembly of cells that continually receives information, analyzes and perceives it and makes decisions. The principle cells of the nervous system are neurons and neuroglial cells. Neurons are the basic communicating units of the nervous system and possess dendrites, axons and synapses required for this role. Neuroglial cells consist of astrocytes, oligodendrocytes, ependymal cells, and microglial cells. Collectively, they are involved in the shelter and maintenance of neurons. The functions of astrocytes are incompletely understood but probably include the provision of biochemical and physical support and aid in insulation of the receptive surfaces of neurons. In addition to their activities in normal brain, they also react to CNS injury by glial scar formation. The principle function of the oligodendrocytes is the production and maintenance of CNS myelin. They contribute segments of myelin sheath to multiple axons.

The ependyma cells react to injury mainly by cell loss. Microglial cells become activated and assume the shape of a macrophage in response to injury or destruction of the brain. These cells can also proliferate and adopt a rod-like form which could surround a tiny focus of necrosis or a dead neuron forming a glial nodule. Microglial degradation of dead neurons is called neuronophagia.

The creatine kinase/creatine phosphate energy system is only one component of an elaborate energy-generating system found in nervous system cells such as, for example, neurons, oligodendrocytes and astrocytes. The components of the creatine energy system include the enzyme creatine kinase, the substrates creatine and creatine phosphate, and the transporter of creatine. The reaction catalyzed by creatine kinase is: $MgADP \pm PCr^{=} + H^{+} \rightleftharpoons MgATP^{=} + Cr$. Some of the functions associated with this system include efficient regeneration of energy in cells with fluctuating and high energy demands, energy transport to different parts of the cell, phosphoryl transfer activity, ion transport regulation, and involvement in signal transduction pathways.

The creatine kinase/phosphocreatine system has been shown to be active in neurons, astrocytes, oligodendrocytes and Schwann cells. Manos et al., *J. Neurochem.* 56:2101-2107 (1991); Molloy et al., *J. Neurochem.* 59:1925-1932.

The activity of the enzyme has been shown to be up-regulated during regeneration and down-regulated in degenerative states (see, e.g., *Annals Neurology* 35(3):331-340 (1994); DeLeon et al., *J. Neuruosci. Res.* 29:437448 (1991); Orlovskaia et al. *Vestnik Rossiiskoi Akademii Meditsinskikh Nauk.* 8:34-39 (1992). Burbaeva et al., *Shurnal Neuropathologll Psikhiatrii Imeni S-S-Korsakova* 90(7):85-87 (1990); Mitochondrial creatine kinase was recently found to be the major constituent of pathological inclusions seen in mitochondrial myopathies. Stadhouders et al., *PNAS*, 91, pp 5080-5093 (1994).

It is an object of the present invention to provide methods for treatment of diseases that affect cells of the nervous system that utilize the creatine kinase/phosphocreatine system using compounds which modulate the system.

SUMMARY OF THE INVENTION

The present invention pertains to methods of treating diseases of the nervous systems in an individual afflicted with such a disease by administering to the afflicted individual an amount of a compound or compounds which modulate one or more of the structural or functional components of the creatine kinase/phosphocreatine system sufficient to prevent, reduce or ameliorate the symptoms of the disease. Compounds which are effective for this purpose include creatine, creatine phosphate, and analogs of creatine or creatine phosphate.

The present invention also provides compositions containing creatine compounds in combination with a pharmaceutically acceptable carrier, and effective amounts of other agents which act on the nervous system, to prophylactically and/or therapeutically treat a subject with a disease of the nervous system. The present invention further pertains to methods of use of creatine compounds in combination with other agents which act on the nervous system for treating diseases of the nervous system.

Packaged drugs for treating subjects having a disease of the nervous system or one who is predisposed to such diseases also are the subject of the present invention. The packaged drugs include a container holding the creatine compound, in combination with a pharmaceutically acceptable carrier, along with instructions for administering the same for the purpose of preventing, ameliorating, arresting or eliminating a disease of the nervous system.

Some of the diseases susceptible to treatment with creatine compounds according to the present invention include, but are not limited to Alzheimer disease, Parkinson's disease, Huntington's disease, motor neuron disease, diabetic and toxic neuropathies, traumatic nerve injury, multiple sclerosis, acute disseminated encephalomyelitis, acute necrotizing hemorrhagic leukoencephalitis, diseases of dysmyelination, mitochondrial diseases, fungal and bacterial infections, migrainous disorders, stroke, aging, dementia, and mental disorders such as depression and schizophrenia

DETAILED DESCRIPTION

The methods of the present invention generally comprise administering to an individual afflicted with a disease of the nervous system an amount of a compound or compounds which modulate one or more of the structural or functional components of the creatine kinase/phosphocreatine system sufficient to prevent, reduce or ameliorate symptoms of the disease. Components of the system which can be modulated include the enzyme creatine kinase, the substrates creatine and creatine phosphate, and the transporter of creatine. As used herein, the term "modulate" means to change, affect or interfere with the normal functioning of the component in the creatine kinase/phosphocreatine enzyme system.

Compounds which are particularly effective for this purpose include creatine, creatine phosphate, and analogs thereof which are described in detail below. The term "creatine compounds" will be used herein to include creatine, creatine phosphate, and compounds which are structurally similar to creatine or creatine phosphate, and analogs of creatine and creatine phosphate. The term "creatine compounds" also includes compounds which "mimic" the activity of creatine, creatine phosphate or creatine analogs, i.e., compounds which inhibit or modulate the creatine kinase system. The term "mimics" is intended to include compounds which may not be structurally similar to creatine but mimic the therapeutic activity of creatine, creatine phosphate or structurally similar compounds. The term "inhibitors of creatine kinase system" are compounds which inhibit the activity of the creatine kinase enzyme, molecules that inhibit the creatine transporter or molecules that inhibit the binding of the enzyme to other structural proteins or enzymes or lipids. The term "modulators of the creatine kinase system" are compounds which modulate the activity of the enzyme, or the activity of the transporter of creatine or the ability of other proteins or enzymes or lipids to interact with the system. The term "creatine analog" is intended to include compounds which are structurally similar to creatine or creatine phosphate, compounds which are art-recognized as being analogs of creatine or creatine phosphate, and/or compounds which share the same or similar function as creatine or creatine phosphate.

The language "treating diseases of the nervous system" is intended to include prevention of the disease, amelioration and/or arrest of a preexisting disease, and the elimination of a preexisting disease. The creatine analogs described herein have both curative and prophylactic effects on disease development and progression.

The language "therapeutically effective amount" is intended to include the amount of the creatine compound sufficient to prevent onset of diseases of the nervous system or significantly reduce progression of such diseases in the subject being treated. A therapeutically effective amount can be determined on an individual basis and will be based, at least in part, on consideration of the severity of the symptoms to be treated and the activity of the specific analog selected if an analog is being used. Further, the effective amounts of the creatine compound may vary according to the age, sex and weight of the subject being treated. Thus, a therapeutically effective amount of the creatine compound can be determined by one of ordinary skill in the art employing such factors as described above using no more than routine experimentation in clinical management.

The language "pharmaceutically acceptable carrier" is intended to include substances capable of being coadministered with the creatine compound and which allows the active ingredient to perform its intended function of preventing, ameliorating, arresting, or eliminating a disease(s) of the nervous system. Examples of such carriers include solvents, dispersion media, adjuvants, delay agents and the like. The use of such media and agents for pharmaceutically active substances is well known in the art. Any conventional media and agent compatible with the creatine compound may be used within this invention.

The term "pharmaceutically acceptable salt" is intended to include art-recognized pharmaceutically acceptable salts. Typically these salts are capable of being hydrolyzed under physiological conditions. Examples of such salts include sodium, potassium and hemisulfate. The term further is intended to include lower hydrocarbon groups capable of being hydrolyzed under physiological conditions, i.e. groups which esterify the carboxyl moiety, e.g. methyl, ethyl and propyl.

The term "subject" is intended to include living organisms susceptible to having diseases of the nervous system, e.g. mammals. Examples of subjects include humans, dogs, cats, horses, cows, goats, rats and mice. The term "subject" further is intended to include transgenic species.

The language "diseases of the nervous system" is intended to include diseases of the nervous system whose onset, amelioration, arrest, or elimination is effectuated by the creatine compounds described herein. Examples of types of diseases of the nervous system include demyelinating, dysmyelinating and degenerative diseases. Examples of locations on or within the subject where the diseases may originate and/or reside include both central and peripheral loci. As the term "disease" is used herein, it is understood to exclude, and only encompass maladies distinct from, neoplastic pathologies and tumors of the nervous system, inschemic injury and viral infections of the nervous system. Examples of types of diseases suitable for treatment with the methods and compounds of the instant invention are discussed in detail below.

Diseases of the Nervous System

Diseases of the nervous system fall into two general categories: (a) pathologic processes such as infections, trauma and neoplasma found in both the nervous system and other organs; and, (b) diseases unique to the nervous system which include diseases of myelin and systemic degeneration of neurons.

Of particular concern to neurologists and other nervous system practitioners are diseases of: (a) demyelination which can develop due to infection, autoimmune antibodies, and macrophage destruction; and, (b) dysmyelination which result from structural defects in myelin.

Diseases of neurons can be the result of: (a) aberrant migration of neurons during embryogenesis and early stage formation; or (b) degenerative diseases resulting from a decrease in neuronal survival, such as occurs in, for example, Alzheimer's disease, Parkinson's disease, Huntington's disease, motor neuron disease, ischemia-related disease and stroke, and diabetic neuropathy.

Demyelinating Diseases:

Primary demyelination is a loss of myelin sheaths with relative preservation of the demyelinated axons. It results either from damage to the oligodendroglia which make the myelin or from a direct, usually immunologic or toxic attack on the myelin itself Secondary demyelination, in contrast, occurs following axonal degeneration. The demyelinating diseases are a group of CNS conditions characterized by extensive primary demyelination. They include multiple sclerosis and its variants and perivenous encephalitis. There are several other diseases in which the principal pathologic change is primary demyelination, but which are usually conveniently classified in other categories such as inborn errors of metabolism, the leukodystrophies, viral disease (progressive multifocal leukoencephalopathy PM), as well as several other rare disorders of unclear etiology.

Multiple Sclerosis (MS)

Multiple sclerosis is a disease of the central nervous system (CNS) that has a peak onset of 30-40 years. It affects all parts of the CNS and causes disability related to visual, sensory, motor, and cerebellar systems. The disease manifestations can be mild and intermittent or progressive and devastating.

The pathogenesis is due to an autoimmune attack on CNS myelin. The treatments available are symptomatic treating spasticity, fatigue, bladder dysfunction, and spasms. Other treatments are directed towards stopping the immunologic attack on myelin. These consist of corticosteroids such as prednisone and methylprednisolone, general immunosuppressants such as cyclophosphamide and azathioprine, and immunomodulating agents such as beta-interferon. No treatments are available to preserve myelin or make it resistant to attacks.

Acute Disseminated Encephalomyelitis

Acute Disseminated Encephalomyelitis usually occurs following a viral infection and is thought to be due to an autoimmune reaction against CNS myelin, resulting in paralysis, lethargy, and coma. It differs from MS by being a monophasic disease whereas MS is characterized by recurrence and chronicity. Treatment consists of administration of steroids.

Acute Necrotizing Hemorrhagic Leukoencephalitis

This is a rare disease that is generally fatal. It is also thought to be mediated by autoimmune attack on CNS myelin that is triggered by a viral infection. Neurologic symptoms develop abruptly with headache, paralysis and coma. Death usually follows within several days. Treatment is supportive.

Leukodystrophies:

These are diseases of the white matter resulting from an error in the myelin metabolism that leads to impaired myelin formation. They are thought of as dysmyelinating diseases, and can become manifest at an early age.

Metachromatic Leukodystrophy: an autosomal recessive (inherited) disorder due to deficiency of the enzyme arylsulfatase A leading to accumulation of lipids. There is demyelination in the CNS and peripheral nervous system leading to progressive weakness and spasticity.

Krabbe's disease: Also inherited as autosomal recessive and due to deficiency of another enzyme: galctocerebroside beta-galactosidase.

Adrenoleukodystrophy and adrenomyeloneuropathy: affect the adrenal glad in addition to the nervous system.

No treatment is available to any of the leukodystrophies except for supportive treatment.

Degenerative Diseases:

There is no good etiology or pathophysiology known for these diseases, and no compelling reason to assume that they all have a similar etiology. Diseases under this category have general similarities. They are diseases of neurons that tend to result in selective impairment, affecting one or more functional systems of neurons while leaving others intact.

Parkinson's Disease:

Parkinson's disease is due to loss of dopaminergic neurones in the substantia nigra of the brain. It is manifested by slowed voluntary movements, rigidity, expressionless face and stooped posture. Several drugs are available to increase dopaminergic function such as levodopa, carbidopa, bromocriptine, pergolide, or decrease cholinergic function such as benztropine, and amantadine. Selegiline is a new treatment designed to protect the remaining dopaminergic neurons.

Spinocerebellar Degenerations

This is a group of degenerative diseases that affects in varying degrees the basal ganglia, brain stem, cerebellum, spinal cord, and peripheral nerves. Patients present symptoms of Parkinsonism, ataxia, spasticity, and motor and sensory deficits reflecting damage to different anatomic areas and/or neuronal systems in the CNS.

Degenerative Disease Affecting Motor Neurons

Included in this category are diseases such as amyotrophic lateral sclerosis (ALS), and spinal muscular atrophy. They are characterized by degeneration of motor neurones in the CNS leading to progressive weakness, muscle atrophy, and death caused by respiratory failure. Treatments are only symptomatic, there are no available treatments to slow down or stop the disease.

Alzheimer Disease (AD):

This disease is characterized clinically by slow erosion of mental function, culminating in profound dementia. The diagnostic pathologic hallmark of AD is the presence of large numbers of senile plagues and neurofibrillary tangles in the brain especially in neocortex and hippocampus. Loss of specific neuron populations in these brain regions and in several subcortical nuclei correlates with depletion in certain neurotransmitters including acetylcholine. The etiology of AD is still unknown. To date a lot of research has focused on the composition and genesis of the B/A4 amyloid component of senile plagues. Alzheimer's disease is characterized clinically by the slow erosion of intellectual function with the development of profound dementia. There are no treatments that slow the progression.

Huntington Disease (HD):

HD is an autosomal dominant disorder of midlife onset, characterized clinically by movement disorder, personality changes, and dementia often leading to death in 15-20 years. The neuropathologic changes in the brain are centered in the basal ganglia. Loss of a class of projection neurons, called "spiny cells" because of their prominent dendritic spinous processes, is typical. This class of cells contains gamma-aminobutyric acid (GABA), substance P, and opioid peptides. Linkage studies have localized the gene for HD to the most distal band of the short arm of chromosome 4. No treatments are available that have been shown to retard progression of the disease. Experimental studies showing a similarity between neurons that are susceptible to N-methyl d-aspartate (NMDA) agonists and those that disappear in HD has led to encouraging speculation that NMDA antagonists might prove beneficial. Some recent studies suggest that a defect in brain energy metabolism might occur in HD and enhance neuronal vulnerability to excitotoxic stress.

Mitochondrial Encephalomyopathies:

Mitochondrial encephalomyopathies are a heterogenous group of disorders affecting mitochondrial metabolism. These deficits could involve substrate transport, substrate utilization, defects of the Krebs Cycle, defects of the respiratory chain, and defects of oxidation/phosphorylation coupling. Pure myopathies vary considerably with respect to age at onset, course (rapidly progressive, static, or even reversible), and distribution of weakness (generalized with respiratory failure, proximal more than distal facioscapulohumeral, orbicularis and extraocular muscles with ptosis and progressive external ophthalmoplegia). Patients with mitochondrial myopathies complain of exercise intolerance and premature fatigue.

Peripheral Nervous System Disorders

The peripheral nervous system (PNS) consists of the motor and sensory components of the cranial and spinal nerves, the autonomic nervous system with its sympathetic and parasympathetic divisions, and the peripheral ganglia. It is the conduit for sensory information to the CNS and effector signals to the peripheral organs such as muscle. Contrary to the brain, which has no ability to regenerate, the pathologic reactions of the PNS include both degeneration and regeneration. There are three basic pathological processes: Wallerian degeneration, axonal degeneration and segmental demyelination that could take place.

Some of the Neuropathic Syndromes Include:

Acute ascending motor paralysis with variable sensory disturbance; examples being acute demyelinating neuropathics, infectious mononucleosis with polyneuritis, hepatitis and polyneuritis, toxic polyneuropathies.

Subacute sensorimotor polyneuropathy; examples of acquired axonal neurophathics include paraproteinemias, uremia diabetes, amyloidosis, connective tissue diseases and leprosy. Examples of inherited diseases include mostly chronic demyelination with hypertrophic changes, such as peroneal muscular atrophy, hypertrophic polyneuropathy and Refsum's diseases.

Chronic relapsing polyneuropathy; such as idiopathic polyneuritis porphyria, Beriberi and intoxications.

Mono or multiple neuropathy; such as pressure palsies, traumatic palsies, serum neuritis, zoster and leprosy.

Creatine Compounds Useful for Treating Nervous System Diseases

Creatine compounds useful in the present invention include compounds which modulate one or more of the structural or functional components of the creatine kinase/phosphocreatine system. Compounds which are effective for this purpose include creatine, creatine phosphate and analogs thereof, compounds which mimic their activity, and salts of these compounds as defined above. Exemplary creatine compounds are described below.

Creatine (also known as N-(aminoiminomethyl)-N-methylglycine; methylglycosamine or N-methyl-guanido acetic acid) is a well-known substance. (See, *The Merck Index*, Eleventh Edition, No. 2570 (1989).

Creatine is phosphorylated chemically or enzymatically by creatine kinase to generate creatine phosphate, which also is well-known (see, *The Merck Index*, No. 7315). Both creatine and creatine phosphate (phosphocreatine) can be extracted from animal tissue or synthesized chemically. Both are commercially available.

Cyclocreatine is an essentially planar cyclic analog of creatine. Although cyclocreatine is structurally similar to creatine, the two compounds are distinguishable both kinetically and thermodynamically. Cyclocreatine is phosphorylated efficiently by creatine kinase in the forward reaction both in vitro and in vivo. Rowley, G. L., *J. Am. Chem. Soc.* 93: 5542-5551 (1971); McLaughlin, A. C. et. al., *J. Biol. Chem.* 247, 4382-4388 (1972).

The phosphorylated compound phosphocyclocreatine is structurally similar to phosphocreatine; however, the phosphorous-nitrogen (P—N) bond of cyclocreatine phosphate is more stable than that of phosphocreatine. LoPresti, P. and M. Cohn, *Biochem. Biophys. Acta* 998: 317-320 (1989); Annesley, T. M. and J. B. Walker, *J. Biol. Chem.* 253; 8120-8125, (1978); Annesley, T. M. and J. B. Walker, Biochem. Biophys. Res. Commun. 74: 185-190 (1977).

Creatine analogs and other agents which act to interfere with the activity of creatine biosynthetic enzymes or with the creatine transporter are useful in the present method of treating nervous system diseases. In the nervous system, there are many possible intracellular, as well as extracellular, sites for the action of compounds that inhibit, increase, or otherwise modify, energy generation through brain creatine kinase and/or other enzymes which are associated with it. Thus the effects of such compounds can be direct or indirect, operating by mechanisms including, but not limited to, influencing the uptake or biosynthesis of creatine, the function of the creatine phosphate shuttle, inhibiting the enzyme activity, or the activity of associated enzymes, or altering the levels of substrates or products of a reaction to alter the velocity of the reaction.

Substances known or believed to modify energy production through the creatine kinase/phosphocreatine system which can be used in the present method are described below. Exemplary compounds are shown in Tables 1 and 2.

TABLE 1

CREATINE ANALOGS

TABLE 1-continued

CREATINE ANALOGS

TABLE 1-continued

CREATINE ANALOGS

TABLE 2

CREATINE PHOSPHATE ANALOGS

TABLE 2-continued

CREATINE PHOSPHATE ANALOGS

It will be possible to modify the substances described below to produce analogs which have enhanced characteristics, such as greater specificity for the enzyme, enhanced stability, enhanced uptake into cells, or better binding activity.

Compounds which modify the structure or function of the creatine kinase/creatine phosphate system directly or indirectly are useful in preventing and/or treating diseases of the nervous system characterized by up regulation or down regulation of the enzyme system.

In diseases where the creatine kinase/creatine phosphate system is down regulated, for example, uncontrolled firing of neurons, molecules useful for treating these diseases include those that will up regulate the activity, or could support energy (ATP) production for a longer period of time. Examples include creatine phosphate and related molecules that form stable phosphagens which support ATP production over a long period of time.

In diseases where the creatine kinase/creatine phosphate system is up regulated, the molecules that are useful include those that will down regulate the activity and/or inhibit energy production (ATP).

Molecules that regulate the transporter of creatine, or the association of creatine kinase with other protein or lipid molecules in the membrane, the substrates concentration creatine and creatine phosphate also are useful in preventing and/or treating diseases of the nervous system.

Compounds which are useful in the present invention can be inhibitors, substrates or substrate analogs, of creatine kinase, which when present, could modify energy generation or high energy phsphoryl transfer through the creatine kinase/phosphocreatine system. In addition, modulators of the enzymes that work in conjunction with creatine kinase now can be designed and used, individually, in combination or in addition to other drugs, to make control of the effect on brain creatine kinase tighter.

The pathways of biosynthesis and metabolism of creatine and creatine phosphate can be targeted in selecting and designing compounds which may modify energy production or high energy phosphoryl transfer through the creatine kinase system. Compounds targeted to specific steps may rely on structural analogies with either creatine or its precursors. Novel creatine analogs differing from creatine by substitution, chain extension, and/or cyclization may be designed. The substrates of multisubstrate enzymes may be covalently linked, or analogs which mimic portions of the different substrates may be designed. Non-hydrolyzable phosphorylated analogs can also be designed to mimic creatine phosphate without sustaining ATP production.

A number of creatine and creatine phosphate analogs have been previously described in the literature or can be readily synthesized. Examples are these shown in Table 1 and Table 2. Some of them are slow substrates for creatine kinase.

Tables 1 and 2 illustrate the structures of creatine, cyclocreatine (1-carboxymethyl-2-iminoimidazolidine), N-phosphorocreatine (N-phosphoryl creatine), cyclocreatine phosphate (3-phosphoryl-1-carboxymethyl-2-iminoimidazolidine) and other compounds. In addition, 1-carboxymethyl-2-aminoimidazole, 1-carboxymethyl-2 2-iminomethylimidazolidine, 1-carboxyethyl-2-iminoimidazolidine, N-ethyl-N-amidinoglycine and b-guanidinopropionic acid are believed to be effective.

Cyclocreatine (1-carboxymethyl-2-iminoimidazolidine) is an example of a class of substrate analogs of creatine kinase, which can be phosphorylated by creatine kinase and which are believed to be active.

A class of creatine kinase targeted compounds are bi-substrate analogs comprising an adenosine-like moiety linked via a modifiable bridge to a creatine link moiety (i.e., creatine or a creatine analog). Such compounds are expected to bind with greater affinity than the sum of the binding interaction of each individual substrate (e.g., creatine and ATP). The modifiable bridge linking an adenosine-like moiety at the 5'-carbon to a creatine like moiety can be a carbonyl group, alkyl (a branched or straight chain hydrocarbon group having one or more carbon atoms), or substituted alkyl group (an alkyl group bearing one or more functionalities, including but not limited to unsaturation, heteroatom-substituents, carboxylic and inorganic acid derivatives, and electrophilic moieties).

Another class of potential compounds for treating nervous system disorders is designed to inhibit (reversibly or irreversibly) creatine kinase. The analogs of creatine in this class can bind irreversibly to the active site of the enzyme. Two such affinity reagents that have previously been shown to completely and irreversibly inactivate creatine kinase are epoxycreatine Marietta, M. A and G. L. Kenyon *J. Biol. Chem.* 254: 1879-1886 (1979)) and isoepoxycreatine Nguyen, A. C. K., Ph.D. dissertation in Pharmaceutical Chemistry, (University of California, San Francisco, 1983), pp. 112-205). There are several approaches to enhancing the specificity and hence, the efficacy of active site-targeted irreversible inhibitors of creatine kinase, incorporating an electrophilic moiety. The effective concentration of a compound required for inhibition can be lowered by increasing favorable and decreasing unfavorable binding contacts in the creatine analog.

N-phosphorocreatine analogs also can be designed which bear non-transferable moieties which mimic the N-phosphoryl group. These cannot sustain ATP production.

Some currently preferred creatine compounds of this invention are those encompassed by the general formula I:

and pharmaceutically acceptable salts thereof, wherein:

a) Y is selected from the group consisting of: $-CO_2H-NHOH$, $-NO_2$, $-SO_3H$, $-C(=O)NHSO_2J$ and $-P(=O)(OH)(OJ)$, wherein J is selected from the group consisting of: hydrogen, $C_1-C_6$ straight chain alkyl, $C_3-C_6$ branched alkyl, $C_2-C_6$ alkenyl, $C_3-C_6$ branched alkenyl, and aryl;

b) A is selected from the group consisting of: C, CH, $C_1-C_5$alkyl, $C_2-C_5$alkenyl, $C_2-C_5$alkynyl, and $C_1-C_5$alkoyl chain, each having 0-2 substituents which are selected independently from the group consisting of:
  1) K, where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0-2 substituents independently selected from the group consisting of: rromo, chloro, epoxy and acetoxy;
  2) an aryl group selected from the group consisting of: a 1-2 ring carbocycle and a 1-2 ring heterocycle, wherein the aryl group contains 0-2 substituents independently selected from the group consisting of: $-CH_2L$ and $-COCH_2L$ where L is independently selected from the group consisting of: bromo, chloro, epoxy and acetoxy; and
  3) $-NH-M$, wherein M is selected from the group consisting of: hydrogen, $C_1-C_4$ alkyl, $C_2-C_4$ alkenyl, $C_1-C_4$ alkoyl, $C_3-C_4$ branched alkyl, $C_3-C_4$ branched alkenyl, and $C_4$ branched alkoyl;

c) X is selected from the group consisting of $NR_1$, $CHR_1$, $CR_1$, O and S, wherein $R_1$ is selected from the group consisting of:
  1) hydrogen;
  2) K where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0-2 substituents independently selected from the group consisting of: bromo, chloro, epoxy and acetoxy;
  3) an aryl group selected from the group consisting of a 1-2 ring carbocycle and a 1-2 ring heterocycle, wherein the aryl group contains 0-2 substituents independently selected from the group consisting of: $-CH_2L$ and $-COCH_2L$ where L is independently selected from the group consisting of: bromo, chloro, epoxy and acetoxy;
  4) a $C_5-C_8$ a-amino-w-methyl-w-adenosylcarboxylic acid attached via the w-methyl carbon;
  5) 2 $C_5-C_8$ a-amino-w-aza-w-methyl-w-adenosylcarboxylic acid attached via the w-methyl carbon; and
  6) a $C_5-C_8$ a-amino-w-thia-w-methyl-w-adenosylcarboxylic acid attached via the w-methyl carbon;

d) $Z_1$ and $Z_2$ are chosen independently from the group consisting of: $=O$, $-NHR_2$, $-CH_2R_2$, $-NR_2OH$; wherein $Z_1$ and $Z_2$ may not both be $=O$ and wherein $R_2$ is selected from the group consisting of:
  1) hydrogen;
  2) K, where K is selected from the group consisting of: $C_1-C_6$ straight alkyl; $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0-2 substituents independently selected from the group consisting of bromo, chloro, epoxy and acetoxy;
  3) an aryl group selected from the group consisting of a 1-2 ring carbocycle and a 1-2 ring heterocycle, wherein the aryl group contains 0-2 substituents independently selected from the group consisting of: $-CH_2L$ and $-COCH_2L$ where L is independently selected from the group consisting of: bromo, chloro, epoxy and acetoxy;
  4) 2 $C_4-C_8$ a-amino-carboxylic acid attached via the w-carbon;
  5) B, wherein B is selected from the group consisting of: $-CO_2H-NHOH$, $-SO_3H$, $-NO_2$, $OP(=O)(OH)(OJ)$ and $-P(=O)(OH)(OJ)$, wherein J is selected from the group consisting of: hydrogen, $C_1-C_6$ straight alkyl, $C_3-C_6$ branched alkyl, $C_2-C_6$ alkenyl, $C_3-C_6$ branched alkenyl, and aryl, wherein B is optionally connected to the nitrogen via a linker selected from the group consisting of $C_1-C_2$ alkyl, $C_2$ alkenyl, and $C_1-C_2$ alkoyl;
  6) -D-E, wherein D is selected from the group consisting of $C_1-C_3$ straight alkyl, $C_3$ branched alkyl, $C_2-C_3$ straight alkenyl, $C_3$ branched alkenyl, $C_1-C_3$ straight alkoyl, aryl and aroyl; and E is selected from the group consisting of: $-(PO_3)_n$NMP, where n is 0-2 and NMP is ribonucleotide monophosphate connected via the 5'-phosphate, 3'-phosphate or the aromatic ring of the base; $-[P(=O)(OCH_3)(O)]_m$-Q, where m is 0-3 and Q is a ribonucleoside connected via the ribose or the aromatic ring of the base; $-[P(=O)(OH)(CH_2)]_m$-Q, where m is 0-3 and Q is a ribonucleoside connected via the ribose or the aromatic ring of the base; and an aryl group containing 0-3 substituents chosen independently from the group consisting of: Cl, Br, epoxy, acetoxy, $-OG$, $-C(=O)G$, and $-CO_2G$, where G is independently selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, $C_4-C_6$ branched alkoyl, wherein E may be attached to any point to D, and if D is alkyl or alkenyl, D may be connected at either or both ends by an amide linkage; and 7) —E, wherein E is selected from the group consisting of —$(PO_3)_n$NMP, where n is 0-2 and NMP is a ribonucleotide monophosphate connected via the 5'-phosphate, 3'-phosphate or the aromatic ring of the base; —$[P(=O)(OCH3)(O)]_m$-Q, where m is 0-3 and Q is a ribonucleoside connected via the ribose or the aromatic ring of the base; —$[P(=O)(OH)(CH_2)]_m$-Q, where m is 0-3 and Q is a ribonucleoside connected via the ribose or the aromatic ring of the base; and an aryl group containing 0-3 substituents chose independently from the group consisting of: Cl, Br, epoxy, acetoxy, —OG, —C(=O)G, and —$CO_2$G, where G is independently selected from the group consisting of: $C_1$-$C_6$ straight alkyl, $C_2$-$C_6$ straight alkenyl, $C_1$-$C_6$ straight alkoyl, $C_3$-$C_6$ branched alkyl, $C_3$-$C_6$ branched alkenyl, $C_4$-$C_6$ branched alkoyl; and if E is aryl, E may be connected by an amide linkage;

e) if $R_1$ and at least one $R_2$ group are present, $R_1$ may be connected by a single or double bond to an $R_2$ group to form a cycle of 5 to 7 members;

f) if two $R_2$ groups are present, they may be connected by a single or a double bond to form a cycle of 4 to 7 members; and g) if $R_1$ is present and $Z_1$ or $Z_2$ is selected from the group consisting of —$NHR_2$, —$CH_2R_2$ and —$NR_2OH$, then $R_1$ may be connected by a single or double bond to the carbon or nitrogen of either $Z_1$ or $Z_2$ to form a cycle of 4 to 7 members.

Creatine, creatine phosphate and many creatine analogs, and competitive inhibitors are commercially available. Additionally, analogs of creatine may be synthesized using conventional techniques. For example, creatine can be used as the starting material for synthesizing at least some of the analogs encompassed by formula I. Appropriate synthesis reagents, e.g. alkylating, alkenylating or alkynylating agents may be used to attach the respective groups to target sites. Alternatively, reagents capable of inserting spacer groups may be used to alter the creatine structure. Sites other than the target site are protected using conventional protecting groups while the desired sites are being targeted by synthetic reagents.

If the creatine analog contains a ring structure, then the analog may be synthesized in a manner analogous to that described for cyclocreatine (Wang, T., *J. Org. Chem*, 39:3591-3594 (1974)). The various other substituent groups may be introduced before or after the ring is formed.

Many creatine analogs have been previously synthesized and described (Rowley et al., *J. Am. Chem. Soc*. 93:5542-5551 (1971); McLaughlin et al., *J. Biol. Chem*. 247:4382-4388 (1972); Nguyen, A. C. K., "Synthesis and enzyme studies using creatine analogs", Thesis, Dept. of Pharmaceutical Chemistry, Univ. Calif, San Francisco (1983); Lowe et al., *J. Biol. Chem*. 225:3944-3951 (1980); Roberts et al., *J. Biol. Chem*. 260:13502-13508 (1985); Roberts et al, *Arch. Biochem. Biophys*. 220:563-571 (1983), and Griffiths et al., *J. Biol. Chem*. 251:2049-2054 (1976)). The contents of all of the forementioned references are expressly incorporated by reference. Further to the forementioned references, Kaddurah-Daouk et al. (WO92/08456; WO90/09192; U.S. Pat. No. 5,324,731; U.S. Pat. No. 5,321,030) also provide citations for the synthesis of a plurality of creatine analogs. The contents of all the aforementioned references and patents are incorporated herein by reference.

Creatine compounds which currently are available or have been synthesized include, for example, creatine, b-guanidinopropionic acid, guanidinoacetic acid, creatine phosphate disodium salt, cyclocreatine, homocyclocreatine, phosphinic creatine, homocreatine, ethylcreatine, cyclocreatine phosphate dilithium salt and guanidinoacetic acid phosphate disodium salt, among others.

Creatine phosphate compounds also can be synthesized chemically or enzymatically. The chemical synthesis is well known. Annesley, T. M. Walker, J. B., *Biochem. Biophys. Res. Commun*., (1977), 74, 185-190; Cramer, F., Scheiffele, E., Vollmar, A., *Chem. Ber*., (1962), 95, 1670-1682.

Salts of the products may be exchanged to other salts using standard protocols. The enzymatic synthesis utilizes the creatine kinase enzyme, which is commercially available, to phosphorylate the creatine compounds. ATP is required by creatine kinase for phosphorylation, hence it needs to be continuously replenished to drive the reaction forward. It is necessary to couple the creatine kinase reaction to another reaction that generates ATP to drive it forward. The purity of the resulting compounds can be confirmed using known analytical techniques including $^1$H NMR, $^{13}$CNMR Spectra, Thin layer chromatography, HPLC and elemental analysis.

Utility

In the present invention, the creatine compounds can be administered to an individual (e.g., a mammal), alone or in combination with another compound, for the treatment of diseases of the nervous system. As agents for the treatment of diseases of the nervous system, creatine compounds can interfere with creatine kinase/phosphocreatine functions, thereby preventing, ameliorating, arresting or eliminating direct and/or indirect effects of disease which contribute to symptoms such as paraplegia or memory impairment. Other compounds which can be administered together with the creatine compounds include neurotransmitters, neurotransmitter agonists or antagonists, steroids, corti-costeroids (such as prednisone or methyl prednisone) immunomodulating agents (such as beta-inteferon), immunosuppressive agents (such as cyclophosphamide or azathioprine), nucleotide analogs, endogenous opioids, or other currently clinically used drugs. When co-administered with creatine compounds, these agents can augment interference with creatine kinase/phosphocreatine cellular functions, thereby preventing, reducing, or eliminating direct and/or indirect effects of disease.

A variety of diseases of the nervous system can be treated with creatine or creatine analogs, including but not limited to those diseases of the nervous system described in detail above. Others include bacterial or fungal infections of the nervous system. Creatine or analogs of creatine can be used to reduce the severity of a disease, reduce symptoms of primary disease episodes, or prevent or reduce the severity of recurrent active episodes. Creatine, creatine phosphate or analogs such as cyclocreatine and cyclocreatine phosphate can be used to treat progressive diseases. Many creatine analogs can cross the blood-brain barrier. For example, treatment can result in the reduction of tremors in Parkinson's disease, and other clinical symptoms.

Modes of Administration

The creatine compound can be administered to the afflicted individual alone or in combination with another creatine analog or other agent. The creatine compounds can be administered as pharmaceutically acceptable salts in a pharmaceutically acceptable carrier, for example. The compound may be administered to the subject by a variety of routes, including, but not necessarily limited to, oral (dietary), transdermal, or parenteral (e.g., subcutaneous, intramuscular, intravenous injection, bolus or continuous infusion) routes of administration, for example. An effective amount (i.e., one that is sufficient to produce the desired effect in an individual) of a composition comprising a creatine analog is administered to the individual. The actual amount of drug to be administered will depend on factors such as the size and age of the individual, in addition to the severity of symptoms, other medical conditions and the desired aim of treatment.

Previous studies have described the administration and efficacy of creatine compounds in vivo. For example, creatine phosphate has been administered to patients with cardiac diseases by intravenous injection. Up to 8 grams/day were administered with no adverse side effects. The efficacy of selected creatine kinase substrate analogs to sustain ATP levels or delay rigor during ischemic episodes in muscle has been investigated. On one study, cyclocreatine was fed to mice, rats and chicks, and appeared to be well-tolerated in these animals. Newly hatched chicks were fed a diet containing 1% cyclocreatine. In the presence of antibiotics, the chicks tolerated 1% cyclocreatine without significant mortality, although the chicks grew more slowly than control chicks (Griffiths, G. R. and J. B. Walker, *J. Biol. Chem.* 251(7): 2049-2054 (1976)). In another study, mice were fed a diet containing 1% cyclocreatine for 10 days (Annesley, T. M. and J. B. Walker, *J. Biol. Chem.* 253(22): 8120-8125 (1978)). Cyclocreatine has been feed to mice at up to 1% of their diet for 2 weeks or for over 4 weeks without gross adverse effects. Lillie et al., *Cancer Res.*, 53: 3172-3178 (1993). Feeding animals cyclocreatine (e.g., 1% dietary) has been shown to lead to accumulation of cyclocreatine in different organs in mM concentrations. For example, cyclocreatine was reported to be taken up by muscle, heart and brain in rats receiving dietary 1% cyclocreatine. Griffiths, G. R. and J. B. Walker, *J. Biol. Chem.* 251(7): 2049-2054 (1976). As shown previously, antiviral activity of cyclocreatine is observed on administering 1% dietary cyclocreatine. Many of the above-referenced studies show that creatine analogs are been shown to be capable of crossing the blood-brain barrier.

The creatine compound can be formulated according to the selected route of administration (e.g., powder, tablet, capsule, transdermal patch, implantable capsule, solution, emulsion). An appropriate composition comprising a creatine analog can be prepared in a physiologically acceptable vehicle or carrier. For example, a composition in tablet form can include one or more additives such as a filler (e.g., lactose), a binder (e.g., gelatin, carboxymethylcellulose, gum arabic), a flavoring agent, a coloring agent, or coating material as desired. For solutions or emulsions in general, carriers may include aqueous or alcoholic/aqueous solutions, emulsions or suspensions, including saline and buffered media. Parenteral vehicles can include sodium chloride, solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Preservatives and other additives can also be present. For example, antimicrobial, antioxidant, chelating agents, and inert gases can be added. (See, generally, Remington's Pharmaceutical Sciences, 16th Edition, Mack, Ed., 1980).

The term "administration" is intended to include routes of administration which allow the creatine compounds to perform their intended function(s) of preventing, ameliorating, arresting, and/or eliminating disease(s) of the nervous system in a subject. Examples of routes of administration which may be used include injection (subcutaneous, intravenous, parenterally, intraperitoneally, etc.), oral, inhalation, transdermal, and rectal. Depending on the route of administration, the creatine-like compound may be coated with or in a material to protect it from the natural conditions which may detrimentally effect its ability to perform its intended function. The administration of the creatine-like compound is done at dosages and for periods of time effective to reduce, ameliorate or eliminate the symptoms of the nervous system disorder. Dosage regimes may be adjusted for purposes of improving the therapeutic or prophylactic response of the compound. For example, several divided doses may be administered daily or the dose may be proportionally reduced as indicated by the exigencies of the therapeutic situation.

In addition, the methods of the instant invention comprise creatine compounds effective in crossing the blood-brain barrier.

The creatine compounds of this invention may be administered alone or as a mixture of creatine compounds, or together with an adjuvant or other drug. For example, the creatine compounds may be coadministered with other different art-recognized moieties such as nucleotides, neurotransmitters, agonists or antagonists, steroids, immunomodulators, immunosuppresants, vitamins, endorphins or other drugs which act upon the nervous system or brain.

Creatine Kinase Isoenzymes in the Brain

Cells require energy to survive and to carry out the multitude of tasks that characterize biological activity. Cellular energy demand and supply are generally balanced and tightly regulated for economy and efficiency of energy use. Creatine kinase plays a key role in the energy metabolism of cells with intermittently high and fluctuating energy requirements such as skeletal and cardiac muscle, brain and neural tissues, including, for example, the retina, spermatozoa and electrocytes. As stated above, the enzyme catalyzes the reversible transfer of the phosphoryl group from creatine phosphate to ADP, to generate ATP. There are multi-isoforms of creatine kinase (CK) which include muscle (CK-MM), brain (CK-BB) and mitochondrial (CK-Mia, CK-Mib) isoforms.

Experimental data suggest that CK is located near the sites in cells where energy generation occurs; e.g., where force generation by motor proteins takes place, next to ion pumps and transporters in membranes and where other ATP-dependent processes take place. It seems to play a complex multi-faceted role in cellular energy homeostasis. The creatine kinase system is involved in energy buffering/energy transport activities. It also is involved in regulating ADP and ATP levels intracellularly as well as ADP/ATP ratios. Proton buffering and production of inorganic phosphate are important parts of the system.

In the brain, this creatine kinase system is quite active. Regional variations in CK activity with comparably high levels in cerebellum were reported in studies using native isoenzyme electrophoresis, or enzymatic CK activity measurements in either tissue extracts or cultured brain cells. Chandler et al. *Stroke*, 19: 251-255 (1988), Maker et al. *Exp. Neurol.*, 38: 295-300 (1973), Manos et al. *J. Neurol. Chem.*, 56: 2101-2107 (1991). In particular, the molecular layer of the cerebellar cortex contains high levels of CK activity (Maker et al. id. (1973) Kahn *Histochem.*, 48: 29-32 (1976) consistent with the recent 3'P-NMR findings which indicate that gray matter shows a higher flux through the CK reaction and higher creatine phosphate concentrations as compared to white matter (Cadoux-Hudson et al. *FASEBJ.*, 3: 2660-2666 (1989), but also high levels of CK activity were shown in cultured oligodendrocytes (Manos et al. id. (1991), Molloy et al. *J. Neurochem.*, 59:1925-1932 (1992), typical glial cells of the white matter. The brain CK isoenzyme CK-BB is the major isoform found in the brain. Lower amounts of muscle creatine kinase (CK-MM) and mitochondrial creatine kinase (CK-Mi) are found.

Localization and Function of CK Isoenzymes in Different Cells of the Nervous System Brain CK (CK-BB) is found in all layers of the cerebellar cortex as well as in deeper nuclei of the cerebellum. It is most abundant in Bergmann glial cells (BGC) and astroglial cells, but is also found in basket cells and neurons in the deeper nuclei. Hemmer et al., *Eur. J. Neuroscience*, 6: 538-549 (1994), Hemmer et al. *Dev. Neuroscience*, 15: 3-5 (1993). The BGC is a specialized type of astroglial cell. It provides the migratory pathway for granule cell migration from the external to the internal granule cell layer during cerebellar development. Another main function of these cells is the proposed ATP-dependent spatial buffering of potassium ions released during the electrical activity of neurons (Newman et al. *Trends Neuroscience*, 8: 156-159 (1985), Reichenbach, Acad. Sci New York, (1991), pp. 272-286. Hence, CK-BB seems to be providing energy (ATP) for migration as well as $K^+$ buffering through regulation of the $Na^+/K^+$ ATPase. The presence of CK-BB in astrocytes (Manos et al. id. 1991, Hemmer et al. id. 1994, Hemmer et al. id. 1993) may be related to the energy requirements of these cells for metabolic interactions with neurons; e.g., tricarboxylic acid cycle (TCA) metabolite and neurotransmitter trafficking. Hertz, *Can J. Physiol. Pharmacol.*, 70: 5145-5157 (1991).

The Purkinje neurons of the cerebellum play a very important role in brain function. They receive excitatory input from parallel fibers and climbing fibers, they represent the sole neuronal output structures of the cerebellar cortex. Calcium mediated depolarizations in Purkinje cell dendrites are thought to play a central role in the mechanism of cerebellar motoric leaning. Ito *Corr. Opin. Neurobiol.*, 1: 616-620 (1991). High levels of muscle CK (CK-MM) were found in Purkinje neurons. Hemmer et al. id. (1994), Hemmer et al., id. (1993). There is strong evidence to support that CK-MM is directly or indirectly coupled to energetic processes needed for $Ca^{++}$ homeostasis or to cellular processes triggered by this second messenger.

The glomerular structures of the cerebellum contain high levels of CK-BB and mitochondrial CK (CK-Mi). Large amounts of energy are needed in these structures for restoration of potassium ion gradients partially broken down during neuronal excitation as well as for metabolic and neurotransmitter trafficking between glial cells and neurons. Hertz et al., id (1991). The presence of CK in these structures may be an indication that part of the energy consumed in these giant complexes might be supported by the creatine kinase system.

In neurons, CK-BB is found in association with synaptic vesicles (Friedhoff and Lerner, *Life Sci.*, 20: 867-872 (1977) as well as with plasma membranes (Lim et al., *J. Neurochem.*, 41: 1177-1182 (1983)).

There is evidence to suggest that CK is bound to synaptic vesicles and to the plasma membrane in neurons may be involved in neurotransmitter release as well as in the maintenance of membrane potentials and the restoration of ion gradients before and after stimulation. This is consistent with the fact that high energy turnover and concomitantly high CK concentrations have been found in those regions of the brain that are rich in synaptic connections; e.g., in the molecular layer of the cerebellum, in the glomerular structures of the granule layer and also in the hippocampus. The observation that a rise in CK levels observed in a fraction of brain containing nerve endings and synapses, parallels the neonatal increase in $Na^+/K^+$ ATPase is also suggestive that higher levels of creatine phosphates and CK are characteristic of regions in which energy expenditure for processes such as ion pumping are large. Erecinska and Silver, *J. Cerebr. Blood Flow and Metabolism*, 9: 2-19 (1989). In addition, protein phosphorylation which plays an important role in brain function is also through to consume a sizable fraction of the total energy available in those cells (Erecinska and Silver, id. 1989). Finally, CK, together with nerve-specific enolase belongs to a group of proteins known as slow component b (SCb). These proteins are synthesized in neuronal cell body and are directed by axonal transport to the axonal extremities. Brady and Lasek, *Cell*, 23: 515-523 (1981), Oblinger et al., *J. Neurol.*, 7: 433-462 (1987) The question of whether CK participates in the actual energetics of axonal transport remains to be answered.

In conclusion, the CK system plays a key role in the energetics of the adult brain. This is supported by $^{31}P$ NMR magnetization transfer measurements showing that the pseudo first order rate constant of the CK reaction in the direction of ATP synthesis as well as CK flux correlate with brain activity which is measured by EEG as well as by the amount of deoxyglucose phosphate formed in the brain after administration of deoxyglucose. The present inventors have discovered that diseases of the nervous system can be treated by modulating the activity of the creatine kinase/creatine phosphate pathway.

The Role of Creatine Kinase in Treating Diseases of the Nervous System

The mechanisms by which nerve cell metabolites are normally directed to specific cell tasks is poorly understood. It is thought that nerve cells, like other cells, regulate the rate of energy production in response to demand. The creatine kinase system is active in many cells of the nervous system and is thought to play a role in the allocation of high energy phosphate to many diverse neurological processes, such as neurotransmitter biosynthesis, electrolyte flux and synaptic communication. Neurological function requires significant energy and creatine kinase appears to play an important role in controlling the flow of energy inside specialized exitable cells such as neurons. The induction of creatine kinase, the BB isozyme and the brain mitochondrial creatine kinase in particular, results in the generation of a high energy state which could sustain or multiply the pathological process in diseases of the nervous system. Creatine kinase induction also causes release of abnormally elevated cellular energy reserves which appear to be associated with certain diseases of the nervous system. Conversely, suppression of the creatine kinase system, or abberances in it, induce a low energy state which could result in or assist in the death in the process of all the nervous system.

The components of the creatine kinase/phosphocreatine system include the enzyme creatine kinase, the substrates creatine and creatine phosphate, and the transporter of creatine. Some of the functions associated with this system include efficient regeneration of energy in cells with fluctuating and high energy demand, phosphoryl transfer activity, ion transport regulation, cytoskeletal association, nucleotide pool preservation, proton buffering, and involvement in signal transduction pathways. The creatine kinase/phosphocreatine system has been shown to be active in neurons, astrocytes, oligodendrocytes, and Schwann cells. The activity of the enzyme has been shown to be up-regulated during regeneration and down-regulated in degenerative states, and aberrant in mitochondrial diseases.

Many diseases of the nervous system are thought to be associated with abnormalities in an energy state which could result in imbalanced ion transport neurotransmitter release and result in cell death. It has been reported that defects in mitochondrial respiration enzymes and glycolytic enzymes may cause impairment of cell function.

Without wishing to be bound by theory, it is thought that if the induction or inhibition of creatine kinase is a cause or a consequence of disease, modulating its activity, may block the disease. Modulating its activity would modulate energy flow and affect cell function. Alternatively, another possibility is that creatine kinase activity generates a product which affects neurological function. For example, creatine phosphate may donate a phosphate to a protein to modify its function (e.g., activity, location). If phosphocreatine is such a phosphate donor, creatine analogs which are phosphorylatable or phosphocreatine analogs may competitively inhibit the interaction of phosphocreatine with a target protein thereby directly or indirectly interfering with nervous system functions. Alternatively, phosphorylatable creatine analogs with altered phosphoryl group transfer potential may tie up phosphate stores preventing efficient transfer of phosphate to targets. A neurological disease could be associated with down regulation of creatine kinase activity. In such cases, replenishment of the substrates, e.g., creatine, creatine phosphate or a substrate analog, which could sustain ATP production for an extended of time, with other activators of the enzyme could be beneficial for treatment of the disease.

Ingestion of creatine analogs has been shown to result in replacement of tissue phosphocreatine pools by synthetic phosphagens with different kinetic and thermodynamic properties. This results in subtle changes of intracellular energy metabolism, including the increase of total reserves of high energy phosphate (see refs. Roberts, J. J. and J. B. Walker, Arch Biochem. Biophys 220(2): 563-571 (1983)). The replacement of phosphocreatine pools with slower acting synthetic phosphagens, such as creatine analogs might benefit neurological disorders by providing a longer lasting source of energy. One such analog, cyclocreatine (1-carboxymethyl-2-aminoimidazolidine) modifies the flow of energy of cells in stress and may interfere with ATP utilization at sites of cellular work.

The pathogenesis of nerve cell death in neurodegenerative diseases is unknown. A significant amount of data has supported the hypothesis that an impairment of energy metabolism may underlie the slow exitotoxic neuronal death. Several studies have demonstrated mitochondrial or oxidative defects in neurodegenerative diseases. Impaired energy metabolism results in decreases in high energy phosphate stores and a deteriorating membrane potential. Under these conditions the voltage sensitive $Mg^{2+}$ block of NMDA receptors is relieved, allowing the receptors to be persistently activated by endogenous concentrations of glutamate. In this way, energy related metabolic defects may lead to neuronal death by a slow exitotoxic mechanism. Recent studies indicate that such a mechanism occurs in vivo, and it may play a role in animal models of Huntington's disease and Parkinson's disease.

As discussed in detail above, the creatine kinase/creatine phosphate energy system is only one component of an elaborate energy-generating system found in the nervous system. The reaction catalyzed by this system results in the rapid regeneration of energy in the form of ATP at sites of cellular work. In the mitochondria the enzyme is linked to the oxidative phosphorylation pathway that has been implicated in diseases of the nervous system. There the enzyme works in the reverse direction where it stores energy in the form of creatine phosphate.

The invention is further illustrated in the following examples, which prove that creatine compounds, represented by creatine itself and the analogue cyclocreatine, are neuroprotective agents in animal models used for neurodegenerative diseases, specifically, Huntington's disease and Parkinson's disease.

EXAMPLES

Example 1

Malonate as a Model of Huntington's Disease

A series of reversible and irreversible inhibitors of enzymes involved in energy generating pathways have been used to generate animal models for neurodegenerative diseases such as Parkinson's and Huntington's diseases.

Inhibitors of the enzyme succinate dehydrogenase which impact cellular energy state have been used successfully to generate a model for Huntington's disease. Brouillet et. al., J. Neurochem., 60: 356-359 (1993); Beal et. al., J. Neurosci. 13: 41814192 (1993); Henshaw et. al., Brain Research 647: 161-166 (1994); Beal et al., J. Neurochem. 61: 1147-1150 (1993). The enzyme succinate dehydrogenase plays a central role in both the tricarboxilic acid cycle as well as the electron transport chain in the mitochindria. It's reversible inhibitor malonate has recently been evaluated in animals. Intrastriatal injections of malonate in rats was shown to produce dose dependent striatal excitotoxic lesions which are attenuated by both competitive and non competitive NMDA antagonist. Henshaw et. al., Brain Research 647: 161-166 (1994). Furthermore the glutamate release inhibitor lamotrigine also attenuates the lesions. Co-injection with succinate blocks the lesions, consistent with an effect on succinate dehydrogenase. The lesions are accompanied by a significant reduction in ATP levels as well as significant increase in lactate levels in vivo as shown by chemical shift resonance imaging. Beal et al., J. Neurochem. 61: 1147-1150 (1993). Further more the increases in lactate are greater in older animals consistent with a marked age-of the lesions. Histological studies have shown that the lesion spares NADPH-diaphorase neurons. Somatostatin concentrations were also spared. In vivo magnetic resonance imaging of lesions shows a significant correlation between increasing lesion size and lactate production.

A series of experiments demonstrated that the administration of coenzyme $Q_{10}$ or nicotinamide produced dose dependent protection against the lesions in the malonate animal model. These compounds attenuated ATP depletions produced by malonate in vivo. Further more the co-administration of coenzyme $Q_{10}$ with nicotinamide attenuated the lesions and reduced increases in lactate which occurred after intrastriatal malonate injections.

All of the above mentioned studies supported malonate as a useful model for the neuropathologic and neurochemical features of Huntington's disease. These lesions produced the same pattern of cellular sparing which is seen in Huntington's disease. There is a depletion of striatal spiny neurons yet a relative preservation of the NADPH diaphorase interneurons. Furthermore there is an increase in lactate concentrations which has been observed in Huntington's disease.

The effect of creatine and it's analogue cyclocreatine were evaluated as representatives of creatine compounds in this malonate model for Huntington's disease. Both compounds were administered orally as 1% of the diet. This mode of administration was based on previous studies were significant build up of compounds in organs high in creatine kinase activity such as the muscle and the brain was demonstrated and were 1% cyclocreatine in the diet was shown to inhibit tumor growth and viral replication. Lillie et al *Cancer Research*, 53: 3172-3178 (1993); Lillie et. al., *Antiviral Research* 23: 203-218 (1994).

Male Sprague-Dawley rats (Charles River, Wilmington, Mass.) weighing around 300 gms were used in this experiment. Animals were divided into three groups, 7 used as controls, 8 treated with creatine and 8 treated with cyclocreatine. Group one was fed regular chow, whereas the other groups were given chow enriched with 1% creatine or cyclocreatine. The compounds were administered for two weeks prior to the administration of malonate and then for a further week prior to sacrifice. Malonate was dissolved in distilled deionized water and the pH was adjusted to 7.4 with 0.1 M HCl. Intrastriatal injections of 1.5 µl of malonate containing 3 µmol were made into the left striatum at the level of the Bregma 2.4 mm lateral to the midline and 4.5 mm ventral to the dura. Animals were sacrificed at 7 days by decapitation and the brains were quickly removed and placed in ice cold 0.9% saline solution. Brains were sectioned at 2 mm intervals in a brain mold. Slices were then placed posterior side down in 2% 2,3,5-tiphenyltetrazolium chloride. Slices were stained in the dark at room temperature for 30 minutes and then removed and placed in 4% paraformaldehyde pH 7.3. Lesions, noted by pale staining, were evaluated on the posterior surface of each section using a Bioquant 4 system by an experienced histologist blinded by experimental conditions. These measurements have been validated by comparing them to measurements obtained on adjacent Nissl stain sections to demonstrate the validity of the method. The data are expressed as the means +/− standard error of means (SEM). Statistical comparisons were made by unpaired Student's t test or one-way analysis of variance with the Fisher protected least significant difference (PLSD) test.

Figure 1:
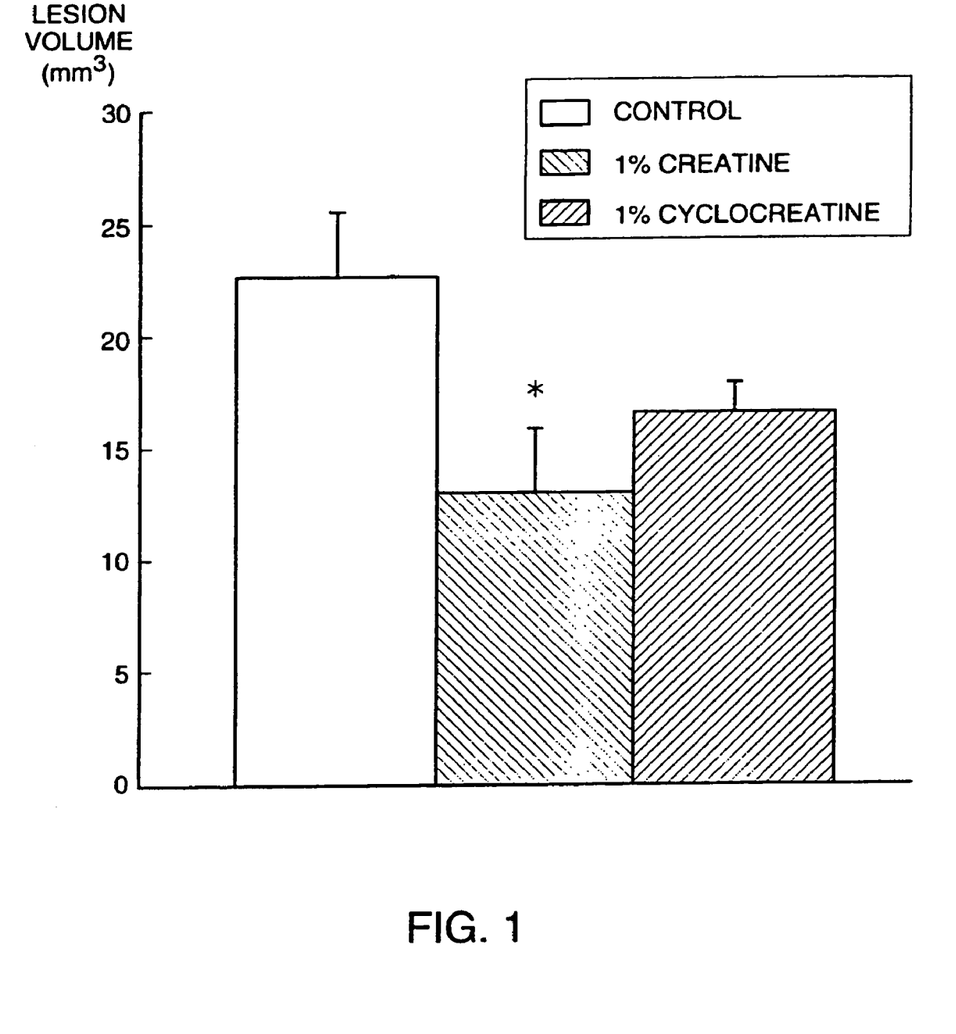
FIG. 1 is a graph illustrating the effect of creatine compounds on lesion volumes in mice using the malonate model.

As shown in FIG. 1, the treatment of animals with creatine produced a significant neuroprotective effect against the intrastriatal injection of malonate. Cyclocreatine also produced some neuroprotective effect. These results implicate the enzyme creatine kinase in pathways involved in neuronal cell death and supports the therapeutic benefit of the creatine compounds in the treatment of neurodegenerative diseases and mitochondrial encephalopathies. Substantial evidence exists for an impairment of mitochondrial energy metabolism in a number of neurodegenerative diseases. This is particularly true in the case of Huntington's disease. The present lesions model Huntington's disease quite well, thus, the results indicate that creatine compounds are useful in slowing the degenerative process in this illness. Other neurodegenerative diseases which were shown to have underlying defects in energy generation also are expected to be slowed by creatine compounds.

Example 2

MPTP as a Model for Parkinson's Disease

MPTP, or 1-methyl-4-phenyl-1,2,3,6-tetrahydropyridine is a neurotoxin which produces a Parkinsonian syndrom in both man and experimental animals. The initial report was by a chemist who was synthesizing and self injecting an opiate analogue. He inadvertently synthesized MPTP and developed profound Parkinsonism. Subsequent pathologic studies showed severe degeneration in the pars compacta of the substantia nigra. A large outbreak subsequently occured in California. These patients developed typical symptoms of Parkinsonism. They also had positron emission tomography done which showed a marked loss of dopaminergic innervation of the stiatum.

Studies of the mechanism of MPTP neurotoxicity show that it involves the generation of a major metabolite, $MPP^+$. This metabolite is formed by the activity of monoamine oxidase on MPTP. Inhibitors of monoamine oxidase block the neurotoxicity of MPTP in both mice and primates. The specificity of the neurotoxic effects of $MPP^+$ for dopaminergic neurons appears to be due to the uptake of $MPP^+$ by the synaptic dopamine transporter. Blockers of this transporter prevent $MPP^+$ neurotoxicity. MPP+has been shown to be a relatively specific inhibitor of mitochondrial complex I activity. It binds to complex I at the retenone binding site. In vitro studies show that it produces an impairment of oxidative phosphorylation. In vivo studies have shown that MPTP can deplete striatal ATP concentrations in mice. It has been demonstrated that MPP+ administered intrastriatally in rats produces significant depletion of ATP as well as increases in lactate confined to the striatum at the site of the injections. The present inventors have recently demonstrated that coenzyme $Q_{10}$ which enhances ATP production can significantly protect against MPTP toxicity in mice.

The effect of two representative creatine compounds, creatine and cyclocreatine, were evaluated using this model. Creatine and cyclocreatine were administered as 1% formulation in the feed of animals and was administered for three weeks before MPTP treatment. MPTP was administered i.p. at a dose of 15 mg/kg every 2 hours for five injections. The animals then remained on either creatine or cyclocreaine supplemented diets for 1 week before sacrifice. The mice examined were male Swiss Webster mice weighing 30-35 grams obtained from Taconic Farms. Control groups recieved either normal saline or MPTP hydrochloride alone. MPTP was administered in 0.1 ml of water. The MPTP was obtained from Research Biochemicals. Eight to twelve animals were examined in each group. Following sacrifice the two striatal were rapidly dissected and placed in chilled 0.1 M perchloric acid. Tissue was subsequently sonicated, and aliquots were taken for protein quantification using a fluorometer assay. Dopamine, 3,4-dihydroxyphenylacetic acid (DOPAC), and homovanillic acid (HVA) were quantified by HPLC with 16 electrode electrochemical detection. Concentrations of dopamine and metabolites were expressed as nmol/mg protein The statistical significance of differences was determined by one-way ANOVA followed by Fisher PLSDpost-hoc test to compare group means.

Figure 2:
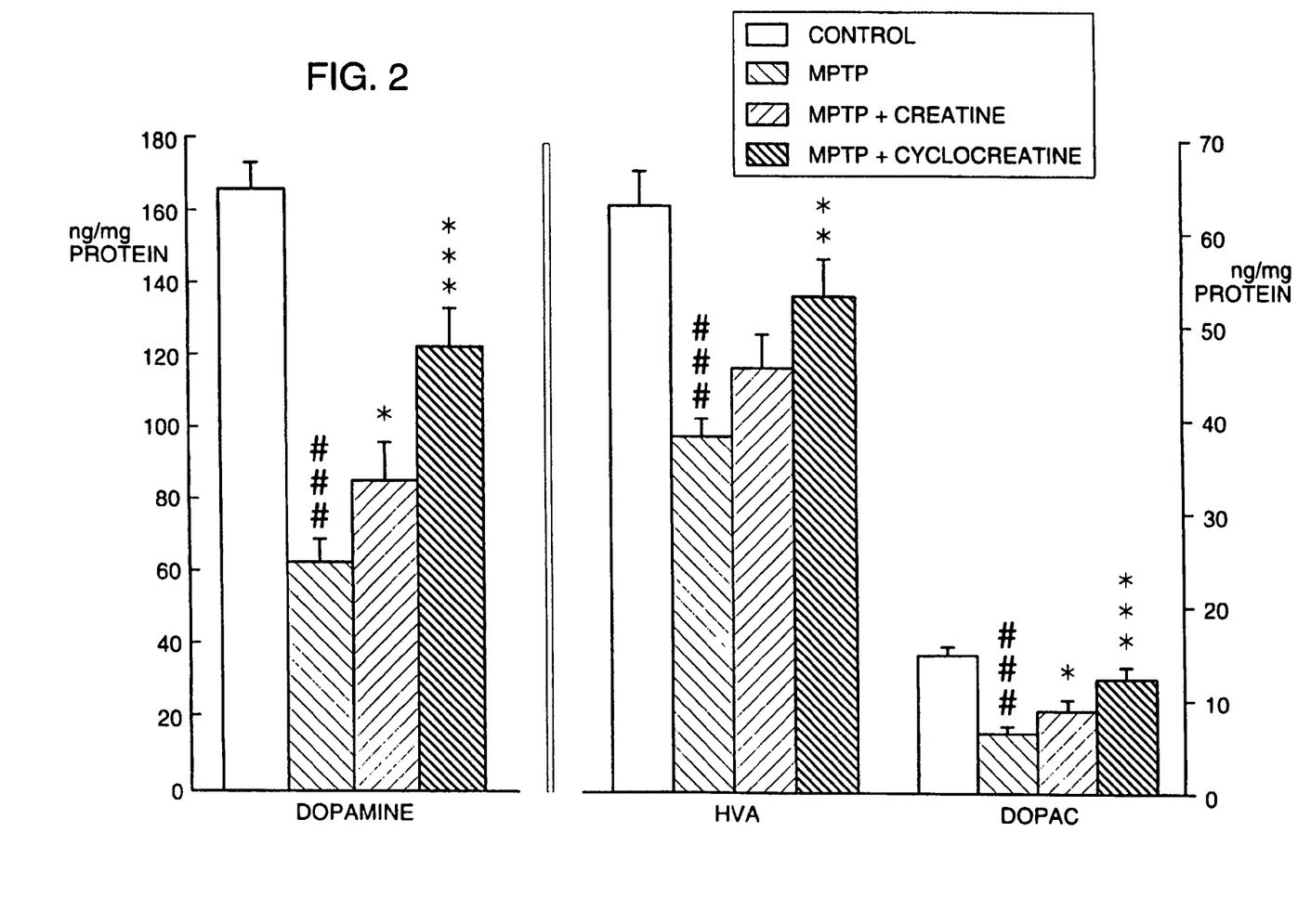
FIG. 2 is a graph illustrating the effect of creatine compounds on levels of dopamine, HVA, and DOPAC in mice using the MPTP animal model.

The results are shown in FIG. 2. Oral administration of either cyclocreatine or creatine significantly protected against DOPAC depletions induced by MPTP. Cyclocreatine was effective against MPTP induced depletions of homovanillic acid. Both administration of creatine and cyclocreatine produce significant neuroprotection against MPTP induced dopamine depletions. The neuroprotective effect produced by cyclocreatine was greater than that seen with creatine alone.

These results indicate that the administration of creatine or cyclocreatine can produce significant neuroprotective effects against MPTP induced dopaminiergic toxicity. These results imply that these compounds are useful for the treatment of Parkinson's disease. The data further establishes the importance of the creatine kinase system in buffering energy and survival of neuronal tissue. Therefor creatine compounds which can sustain energy production in neurons are going to emerge as a new class of protective agents of benefit therapeutically in the treatment of neurodegenerative diseases where impairment of energy has been established.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating a subject afflicted with amyotrophic lateral sclerosis, comprising administering to the subject an amount of creatine, such that the subject is treated for amyotrophic lateral sclerosis.

2. The method of claim 1, wherein said subject is a human.

3. A method for treating a subject afflicted with amyotrophic lateral sclerosis, comprising administering to the subject an amount of creatine phosphate, such that the subject is treated for amyotrophic lateral sclerosis.

4. The method of claim 3, wherein said subject is a human.

5. A method for reducing progression of amyotrophic lateral sclerosis in a subject, comprising administering to the subject an amount of creatine, such that the progression of amyotrophic lateral sclerosis in said subject is reduced.

6. The method of claim 5, wherein said subject is a human.

7. A method for reducing progression of amyotrophic lateral sclerosis in a subject, comprising administering to the subject an amount of creatine phosphate, such that the progression of amyotrophic lateral sclerosis in said subject is reduced.

8. The method of claim 7, wherein said subject is a human.

* * * * *